US012678810B2

(12) United States Patent
Fujii et al.

(10) Patent No.: US 12,678,810 B2
(45) Date of Patent: Jul. 14, 2026

(54) SPRAY IONIZATION DEVICE

(71) Applicant: National Institute of Advanced Industrial Science and Technology, Tokyo (JP)

(72) Inventors: Shinichiro Fujii, Tsukuba (JP); Kazumi Inagaki, Tsukuba (JP); Shinichi Miyashita, Tsukuba (JP)

(73) Assignee: NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 922 days.

(21) Appl. No.: 17/795,113

(22) PCT Filed: Oct. 28, 2020

(86) PCT No.: PCT/JP2020/040419
§ 371 (c)(1),
(2) Date: Jul. 25, 2022

(87) PCT Pub. No.: WO2021/157142
PCT Pub. Date: Aug. 12, 2021

(65) Prior Publication Data
US 2023/0063626 A1 Mar. 2, 2023

(30) Foreign Application Priority Data
Feb. 3, 2020 (JP) ................................. 2020-016414

(51) Int. Cl.
B05B 5/03 (2006.01)
A61L 9/22 (2006.01)
(Continued)

(52) U.S. Cl.
CPC .................. B05B 5/03 (2013.01); A61L 9/22 (2013.01); B05B 5/001 (2013.01); B05B 5/0255 (2013.01); B05B 5/0533 (2013.01); H01J 49/165 (2013.01)

(58) Field of Classification Search
CPC ........... B05B 5/01; B05B 5/255; B05B 5/533; B05B 5/03; H01J 49/165; H01J 49/167; H01J 49/45
See application file for complete search history.

(56) References Cited

U.S. PATENT DOCUMENTS 3,735,925 A * 5/1973 Benedek ................... B05B 5/03
118/621
4,018,973 A * 4/1977 Paton ...................... F27D 11/08
373/21
(Continued)

FOREIGN PATENT DOCUMENTS

CN        107238654 A     10/2017
EP          3971564 A1      3/2022
(Continued)

OTHER PUBLICATIONS

Extended European Search Report mailed Sep. 15, 2023, issued in the EP Patent Application No. 20917599.1.
(Continued)

*Primary Examiner* — Joseph A Greenlund
(74) *Attorney, Agent, or Firm* — Troutman Pepper Locke LLP; James E. Armstrong, IV

(57) ABSTRACT
A spray ionization device comprising: a first tube that has a first flow path through which a liquid can flow and a first outlet on one end thereof from which the liquid is sprayed; a second tube that surrounds the first tube with a gap therebetween, has a second flow path through which a gas can flow, and has a second outlet on the one end thereof; and an electrode that extends through the interior of the first flow
(Continued)

path of the first tube, from the other end thereof to the one end, said electrode being arranged such that the tip thereof is at the same position as the first outlet or is further on the other end side than the first outlet, and said electrode being able to apply a voltage to the liquid by means of a power source connected to the electrode.

13 Claims, 13 Drawing Sheets

(51) Int. Cl.

| | |
|---|---|
| *B05B 5/00* | (2006.01) |
| *B05B 5/025* | (2006.01) |
| *B05B 5/053* | (2006.01) |
| *H01J 49/16* | (2006.01) |

(56) References Cited

U.S. PATENT DOCUMENTS

| | | | | |
|---|---|---|---|---|
| 4,508,265 | A * | 4/1985 | Jido | B05B 5/03 |
| | | | | 239/3 |
| 4,575,609 | A * | 3/1986 | Fassel | B23K 10/00 |
| | | | | 239/424.5 |
| 4,775,774 | A * | 10/1988 | Caneer, Jr. | H05H 1/3405 |
| | | | | 219/121.54 |
| 5,928,731 | A * | 7/1999 | Yanagida | B05B 5/0533 |
| | | | | 427/486 |
| 5,992,244 | A * | 11/1999 | Pui | B01J 19/088 |
| | | | | 73/865.5 |
| 6,586,731 | B1 * | 7/2003 | Jolliffe | H01J 49/049 |
| | | | | 250/281 |
| 7,145,137 | B2 * | 12/2006 | Montaser | H01J 49/105 |
| | | | | 250/288 |
| 7,671,329 | B2 * | 3/2010 | Sakata | H01J 49/105 |
| | | | | 250/281 |
| 7,960,711 | B1 * | 6/2011 | Sheehan | H01J 49/165 |
| | | | | 250/493.1 |
| 8,272,576 | B2 * | 9/2012 | Doak | B05B 7/0475 |
| | | | | 239/128 |
| 8,772,709 | B2 * | 7/2014 | Moeller | H01J 49/167 |
| | | | | 250/281 |
| 8,809,777 | B2 * | 8/2014 | Bajic | G01N 30/724 |
| | | | | 250/288 |
| 9,165,751 | B1 * | 10/2015 | Schleifer | G01N 1/28 |
| 9,768,004 | B2 * | 9/2017 | Fogwill | H01J 49/10 |
| 11,705,318 | B2 * | 7/2023 | Bajic | H01J 49/167 |
| | | | | 250/282 |
| 11,826,770 | B2 * | 11/2023 | Inagaki | G01N 21/714 |
| 11,944,993 | B1 * | 4/2024 | Burgener | B05B 7/0815 |
| 2008/0173327 | A1 * | 7/2008 | Miyagi | B05B 7/0433 |
| | | | | 204/661 |
| 2009/0250608 | A1 * | 10/2009 | Mordehai | H01J 49/167 |
| | | | | 250/288 |
| 2010/0271631 | A1 | 10/2010 | Schluter et al. | |
| 2010/0317118 | A1 * | 12/2010 | Masujima | C12M 47/06 |
| | | | | 436/63 |
| 2014/0023856 | A1 * | 1/2014 | Bisges | C23C 4/12 |
| | | | | 428/328 |
| 2014/0353495 | A1 * | 12/2014 | Inagaki | H01J 49/105 |
| | | | | 239/398 |
| 2015/0206729 | A1 * | 7/2015 | Inagaki | H01J 49/045 |
| | | | | 250/288 |
| 2016/0172178 | A1 * | 6/2016 | Apffel | H01J 49/168 |
| | | | | 250/336.1 |
| 2017/0025262 | A1 * | 1/2017 | Xu | G01N 27/447 |
| 2019/0341241 | A1 * | 11/2019 | Kaushal | H01J 49/045 |
| 2020/0234940 | A1 * | 7/2020 | Fukui | H01J 49/165 |
| 2021/0210320 | A1 * | 7/2021 | Bajic | H01J 49/045 |
| 2022/0001405 | A1 * | 1/2022 | Inagaki | B05B 5/03 |
| 2022/0305505 | A1 * | 9/2022 | Fujii | B05B 5/0426 |
| 2023/0051469 | A1 * | 2/2023 | Fujii | B05B 5/03 |
| 2023/0063626 | A1 * | 3/2023 | Fujii | B05B 7/066 |

FOREIGN PATENT DOCUMENTS

| | | | |
|---|---|---|---|
| EP | 3951379 | B1 | 11/2023 |
| EP | 3971564 | B1 | 4/2024 |
| JP | 2001-357815 | A | 12/2001 |
| JP | 2005-270669 | A | 10/2005 |
| JP | 2010-530795 | A | 9/2010 |
| JP | 2012-089268 | A | 5/2012 |
| WO | 2008/142393 | A1 | 11/2008 |
| WO | 2009/063776 | A1 | 5/2009 |
| WO | 2019/065405 | A1 | 4/2019 |
| WO | 2019/219748 | A1 | 11/2019 |

OTHER PUBLICATIONS

Extended European Search Report dated Jul. 30, 2024, issued in the EP Patent Application No. 24171250.4.

* cited by examiner

SPRAY IONIZATION DEVICE

BACKGROUND OF THE INVENTION

Technical Field

The present invention relates to a spray ionization device.

Background Art

A mass spectrometer can count ions constituting a substance by each mass-to-charge ratio to obtain ionic strength which is quantitative information on the substance. The mass spectrometer can perform more accurate analysis by obtaining ionic strength having a favorable signal-to-noise ratio. Therefore, an analysis target, which is an ionized or charged material, needs to be sufficiently introduced.

Examples of a method of ionizing a liquid sample include an electrospray ionization method. With the electrospray ionization method, high voltage of several kilovolts is applied to a sample solution in a narrow tube, a liquid cone (so-called Taylor cone) is formed at the tip of an outlet port, electrically charged droplets are ejected from the tip, solvents evaporate to reduce the volume of the electrically charged droplets, and the droplets finally split apart to generate gas-phase ions. This method can form electrically charged droplets at a rate of ejecting 1 to 10 µL/min of solution, in which the eject rate is not sufficient for use in conjunction with a liquid chromatography method.

A gas spray assisted electrospray ionization method (see, for example, U.S. Pat. No. 8,809,777) may be an example of a method for supporting generation of electrically charged droplets and vaporization of solvents by ejecting a gas from an outer tube surrounding a narrow tube of a sample solution, in order to promote vaporization of electrically charged droplets.

Patent Document 1: U.S. Pat. No. 8,809,777, Specification

SUMMARY OF THE INVENTION

Problems to be Solved by the Invention

However, the gas spray assisted electrospray ionization method as disclosed in U.S. Pat. No. 8,809,777 generates electrically charged droplets having a large particle size; therefore, there is a need to use techniques such as promoting vaporization of solvents by using a heated gas, atomizing electrically charged droplets by collision with a plate-shaped target, or making the ejection direction orthogonal to the direction of introducing the atomized and electrically charged droplets in order to remove excessively large electrically charged droplets; as a result, electrically charged droplets cannot be efficiently obtained, which has been a problem.

One object of the present invention is to solve the aforementioned problems and provide a spray ionization device capable of efficiently obtaining atomized and electrically charged droplets to be ejected.

Means for Solving the Problems

One aspect of the present invention provides a spray ionization device, including: a first tube including a first channel through which a liquid can flow, the first tube including a first outlet for ejecting the liquid at one end; a second tube surrounding the first tube with a gap and including a second channel through which a gas can flow, the second tube including a second outlet at the one end, the second channel being defined by an outer circumferential surface of the first tube and an inner circumferential surface of the second tube; and an electrode which extends within a first channel of the first tube from an opposite end to the first end, and is arranged so that a leading end is the same position as the first outlet or further toward the opposite end than the first outlet, the electrode being capable of applying voltage to the liquid by way of a power source connected to the electrode, in which at the one end, the second outlet is arranged further toward a tip than the first outlet, at least a portion of the inner circumferential surface of the second tube has a diameter that progressively decreases toward the second outlet, and a diameter of the inner circumferential surface of the second outlet is equal to or greater than an opening diameter of the first outlet, and electrically charged droplets of the liquid can be ejected from the second outlet.

According to the aforementioned aspect, the flow of droplets of the liquid ejected from the first outlet of the first tube focuses while being enveloped in the gas flowing through the second channel of the second tube. As a result, droplets of the liquid can be prevented from contacting the inner circumferential surface of the second tube near the first outlet of the first tube, whereby clogging can be avoided. The flow of droplets of the ejected liquid focuses by the gas, whereby the droplets are atomized. The charged and atomized droplets are formed by voltage being applied to the liquid by the electrode extending within the first channel from the opposite end to the one end and the leading end and arranged so that the leading end becomes the same position as the first outlet or further to the opposite side than the first outlet, until flowing from the opposite end through the first channel and is sprayed from the first outlet. Therefore, a spray ionization device, which is capable of efficiently obtaining atomized and electrically charged droplets to be ejected, can be provided.

Another aspect of the present invention provides a spray ionization device, including: a first tube including a first channel through which a liquid can flow, the first tube including a first outlet for ejecting the liquid at one end; a second tube surrounding the first tube with a gap and including a second channel through which a gas can flow, the second tube including a second outlet arranged further toward a tip than the first outlet at the one end, the second channel being defined by an outer circumferential surface of the first tube and an inner circumferential surface of the second tube; an electrode that extends within a first channel of the first tube, and is arranged so that a leading end is the same position as the first outlet or further toward the opposite end than the first outlet, the electrode capable of applying voltage to the liquid by way of a power source connected to the electrode; and a reticulated member covering the second outlet, or an opening provided to the second tube between the first outlet and the second outlet, the opening being narrower than an opening of the first outlet, wherein electrically charged droplets of the liquid can be ejected from the second outlet.

According to the aforementioned aspect, the liquid ejected from the first outlet of the first tube and the gas having flowed through the second channel collide with the reticulated member, or collide with each other at high speed in the region between the first outlet and the opening, whereby droplets are atomized. The charged and atomized droplets are formed by voltage being applied to the liquid by the electrode extending within the first channel from the opposite end to the one end and the leading end and arranged so that the leading end becomes the same position as the first outlet or further to the opposite side than the first outlet, until flowing from the opposite end through the first channel and is sprayed from the first outlet. Therefore, a spray ionization device, which is capable of efficiently obtaining atomized and electrically charged droplets to be ejected, can be provided.

BRIEF DESCRIPTION OF THE DRAWINGS

FIG. 6 is a cross-sectional view of a nozzle of a second variation of the sprayer of the first embodiment of the present invention;

PREFERRED MODE FOR CARRYING OUT THE INVENTION

Figure 1:
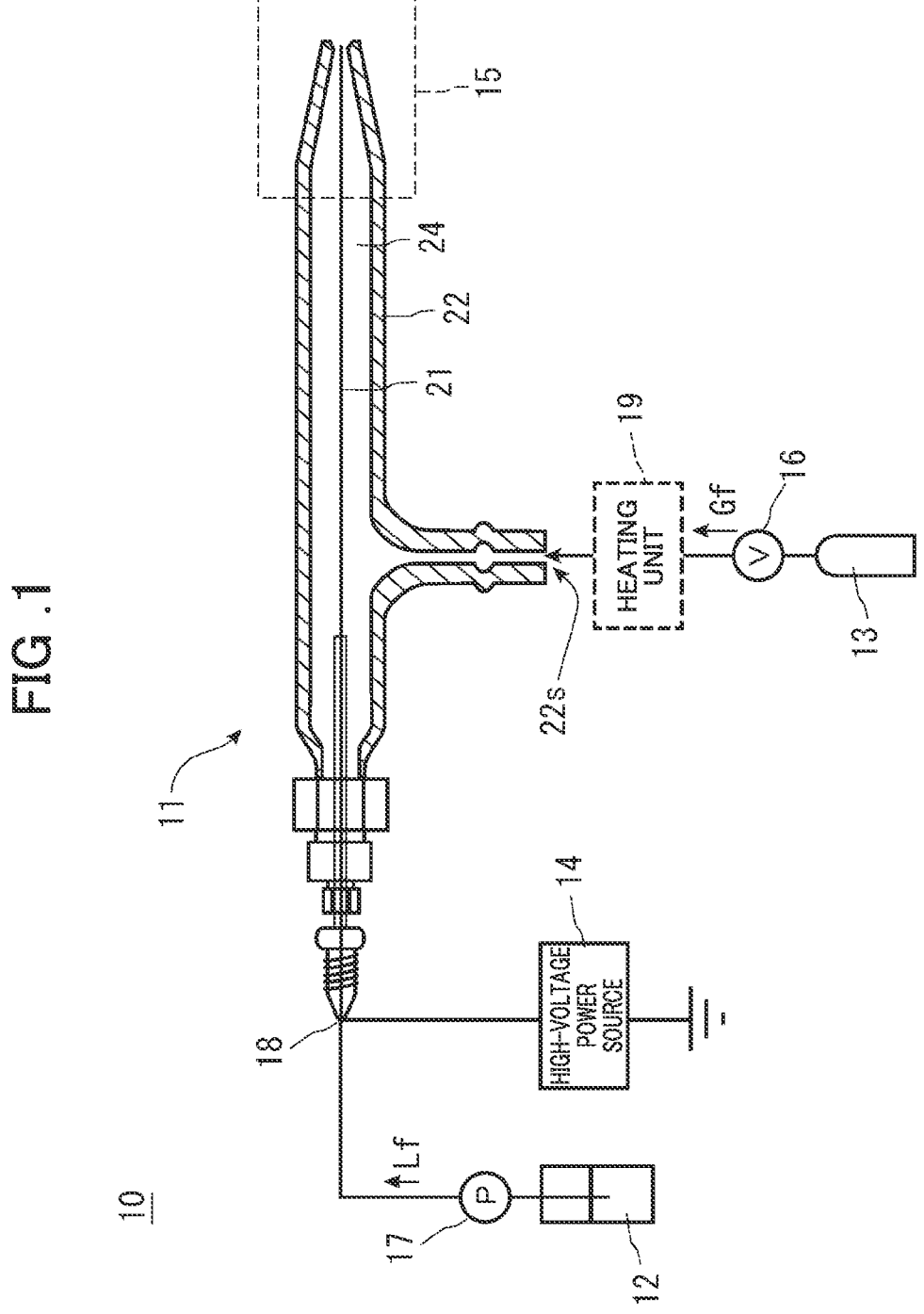
FIG. 1 is a diagram schematically illustrating a configuration of a spray ionization device according to a first embodiment of the present invention.

Hereinafter, embodiments of the present invention will be described with reference to the drawings. Note that elements that are common between a plurality of drawings are denoted by the same reference characters, and detailed description of such elements will not be repeated.

FIRST EMBODIMENT

Figure 2A:
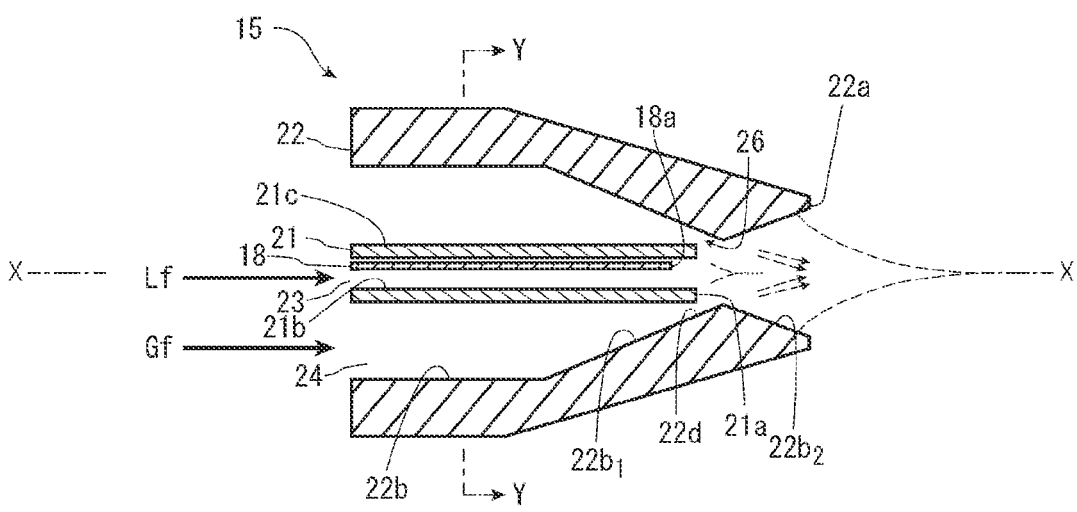
FIGS. 2A and 2B are cross-sectional views of a nozzle of a sprayer according to the first embodiment of the present invention.
Figure 2B:
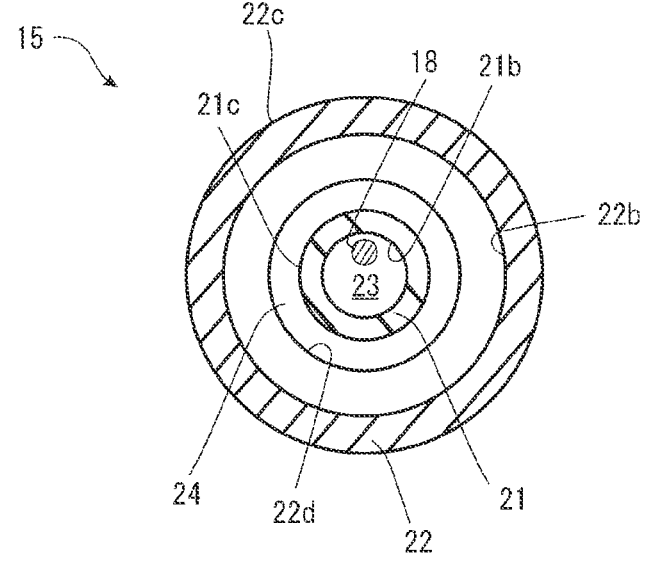

FIG. 1 is a diagram schematically illustrating a configuration of a spray ionization device according to a first embodiment of the present invention. FIGS. 2A and 2B are cross-sectional views of a nozzle of a sprayer, in which FIG.

2A is an enlarged cross-sectional view of the nozzle of FIG. 1, and FIG. 2B is a view along arrows Y-Y in FIG. 2A.

Referring to FIGS. 1, 2A and 2B, a spray ionization device 10 according to a first embodiment of the present invention includes: a sprayer 11; a container 12 containing a sample liquid Lf to be supplied to the sprayer 11; a cylinder 13 for containing a spraying gas Gf to be supplied to the sprayer 11; and a high-voltage power source 14 for applying high voltage to the sample liquid Lf via an electrode 18. In the spray ionization device 10, a nozzle 15 for ejecting electrically charged droplets is formed at one end (hereinafter also referred to as an ejection end) of the sprayer 11. The sample liquid Lf and the spraying gas Gf are supplied from further toward the opposite end than the nozzle 15 (hereinafter also referred to as a supply end). The sample liquid Lf may be continuously or intermittently supplied from the container 12 by way of a pump 17 or the like. The sample liquid Lf may contain an analysis target in solvents, or may contain dissolved components, particulate matter, or the like, for example. The spraying gas Gf is supplied from the cylinder 13 through the valve 16 to the supply port 22s. Inert gas such as nitrogen gas or argon gas, or air can be used for the spraying gas Gf, for example. A heating unit 19 such as a heater or dryer for heating the spraying gas Gf may be provided between the cylinder 13 or the valve 16 and the supply port 22s. The spraying gas Gf is heated, whereby vaporization of solvents in the ejected sample liquid Lf can be promoted, and electrically charged droplets can be obtained more efficiently.

The sprayer 11 includes a liquid supply tube 21 and a gas supply tube 22 that surrounds the liquid supply tube 21 with a gap. The liquid supply tube 21 and the gas supply tube 22 have a double tube structure, in which the tubes are preferably coaxial (central axis X-X) with one another.

The liquid supply tube 21 extends from the supply end to the ejection end. The liquid supply tube 21 includes a first channel 23 being tubular and defined by an inner circumferential surface 21b of the liquid supply tube 21, and includes an outlet 21a of the nozzle 15 at the ejection end. A diameter (inner diameter) of the inner circumferential surface 21b of the liquid supply tube 21 is preferably 10 μm to 250 μm, and a diameter (outer diameter) of an outer circumferential surface 21c of the liquid supply tube 21 is preferably 100 μm to 400 μm. In terms of atomizing droplets, an opening diameter of the outlet 21a is preferably 0.2 μm to 150 μm. In terms of atomizing droplets, the thickness (wall thickness) of the liquid supply tube 21 is preferably 1 μm to 50 μm.

The liquid supply tube 21 is preferably formed from dielectric material made of glass and plastic. In the first channel 23 within the liquid supply tube 21, the electrode 18 is provided as described later.

The gas supply tube 22 includes a second channel 24 defined by an inner circumferential surface 22b of the gas supply tube 22 and the outer circumferential surface 21c of the liquid supply tube 21, and includes an outlet 22a of the nozzle 15. Although not limited in particular, a diameter (inner diameter) of the inner circumferential surface 22b of the gas supply tube 22 is, for example, 4 mm further toward the supply end than the nozzle 15.

The gas supply tube 22 is made of a dielectric material such as glass or plastics, and is preferably made of silica glass, in particular, fused silica glass.

The spraying gas Gf is pressurized and supplied from the supply port 22s of the gas supply tube 22, flows through the second channel 24, and is ejected from the outlet 22a. A flow rate of the spraying gas Gf is appropriately set in accordance with the flow rate of the sample liquid Lf, and is set to 0.5 L/min to 5.0 L/min, for example.

The high-voltage power source 14 is a power source for generating high-voltage direct current voltage, and is connected to the electrode 18 arranged so as to be able to contact the sample liquid Lf flowing through the sprayer 11. The high-voltage power source 14 applies voltage of e.g., 4 kV to the electrode 18, and preferably applies voltage in a range of 0.5 kV to 10 kV in terms of ionization.

The electrode 18 extends in the first channel 23 of the liquid supply tube 21 from the supply side to ejection side, and a leading end 18a is arranged at the same position as the outlet 21a or further towards the supply side than the outlet 21a. Since the electrode 18 can thereby generate a strong electric field by high voltage applied in the vicinity of the outlet 21a, electrostatic spray of the sample liquid Lf becomes possible. In the electrode 18, the leading end 18a is preferably closer to the outlet 21; however, it is preferably arranged so as not to project downstream from the outlet 21a. In terms of atomizing droplets, the electrode 18 preferably has the leading end 18a arranged in the range of 0 μm to 500 μm to the supply side from the outlet 21a. In terms of superior corrosion resistance, the electrode 18 is preferably formed from a platinum group metal, gold or an alloy of these. In addition, the electrode 18 may be formed from common electrode materials such as titanium and tungsten. In terms of being able to easily arrange within the first channel 23, the electrode 18 is preferably a wire of the above-mentioned material.

In the nozzle 15, the outlet 22a of the gas supply tube 22 is arranged further toward the distal end than the outlet 21a of the liquid supply tube 21. The gas supply tube 22 is formed such that a portion 22b1 of the inner circumferential surface of the gas supply tube 22 has a diameter that progressively decreases from upstream toward downstream, whereby the channel area of the second channel 24 progressively decreases. Here, the channel area refers to an area occupied by the second channel 24 on a plane perpendicular to the central axis X, in which the area is surrounded by the inner circumferential surface 22b of the gas supply tube 22 and the outer circumferential surface 21c of the liquid supply tube 21 as illustrated in FIG. 2B. The gas supply tube 22 is formed such that the diameter of the inner circumferential surface of the outlet 22a of the gas supply tube 22 is equal to or larger than the opening diameter of the outlet 21a of the surface liquid supply tube 21. With such a configuration, droplets of the sample liquid Lf are ejected from the outlet 21a of the liquid supply tube 21, enveloped in the spraying gas Gf flowing through the second channel 24, and flow in the X-axis direction while focusing along the X-axis in the central direction. As a result, droplets of the sample liquid Lf are suppressed from contacting the inner circumferential surface 22b2 of the gas supply tube 22 in the vicinity of the outlet 21a of the liquid supply tube 21, whereby the nozzle 15 can be prevented from clogging. The flow of the ejected sample liquid Lf focuses by the spraying gas Gf, whereby droplets are atomized. Since the electrode 18 applies high voltage supplied from the high-voltage power source 14 to the sample liquid Lf, the ejected and atomized droplets have been charged. In this manner, the spray ionization device 10 can eject atomized and electrically charged droplets.

The nozzle 15 of the sprayer 11 preferably includes a constriction portion 26 in the second channel 24, in which the channel area of the second channel 24 is the smallest. The constriction portion 26 is provided to a portion 22d, in which the inner circumferential surface 22b1 of the gas supply tube 22 has a diameter that progressively decreases from upstream toward downstream, and the distance between the inner circumferential surface 22b1 and the outer circumferential surface 21c of the liquid supply tube 21 is the smallest. In the constriction portion 26, a distance between the portion 22d of the inner circumferential surface 22b1 of the gas supply tube 22 and the outer circumferential surface 21c of the liquid supply tube 21 is preferably set to 5 μm to 20 μm.

This arrangement increases the pressure of the spraying gas Gf flowing through the second channel 24 at the constriction portion 26, increases the flow rate (linear velocity) of the spraying gas Gf having passed through the constriction portion 26, and promoting the atomization of the sample liquid Lf ejected from the outlet 21a of the liquid supply tube 21. Droplets ejected from the outlet 21a of the liquid supply tube 21 can be further suppressed from flowing backward through the second channel 24 and entering the constriction portion 26. As a result, clogging of the constriction portion 26 due to precipitation of components such as salts contained in droplets can be suppressed, whereby stable ejection can be achieved. This constriction portion 26 achieves a flow-focusing effect, in which droplets ejected from the outlet 21a can be ejected at a narrower angle (i.e., in a smaller lateral spreading range with respect to the ejection direction) than the case without the constriction portion 26. As a result, efficiency of generating gas phase ions in the ejected and electrically charged droplets can be enhanced.

The diameter of the inner circumferential surface 22b2 of the gas supply tube 22 in the vicinity of the outlet 22a may progressively increase from the portion 22d of the constriction portion 26 toward the outlet 22a. As a result, the channel area of the second channel 24 is progressively widened toward the outlet 22a. As a result, the flow of the spraying gas Gf can be suppressed from being disturbed, and the flow of the ejected, atomized and electrically charged droplets can be suppressed from spreading laterally with respect to the ejection direction.

The outer circumferential face 21c of the liquid supply tube 21, has an outer diameter formed to be constant towards the outlet 21a, whereby the flow of spraying gas Gf converges the ejected sample liquid Lf at the outlet 21a of the liquid supply tube 21, and it is possible to suppress splashing of the sample liquid Lf and effectively form droplets. It should be noted that the end face of the outlet 21a may be formed so as to progressively decrease in diameter from the upstream side towards the outlet 21a.

The outlet 21a of the liquid supply tube 21 preferably has an opening diameter smaller than the diameter of the inner circumferential surface 22b of the gas supply tube 22 at the constriction portion 26. As a result, the spraying gas Gf having passed through the constriction portion 26 can form a flow so as to envelop the flow of droplets of the sample liquid Lf, in the outlet 21a of the liquid supply tube 21.

Figure 3A:
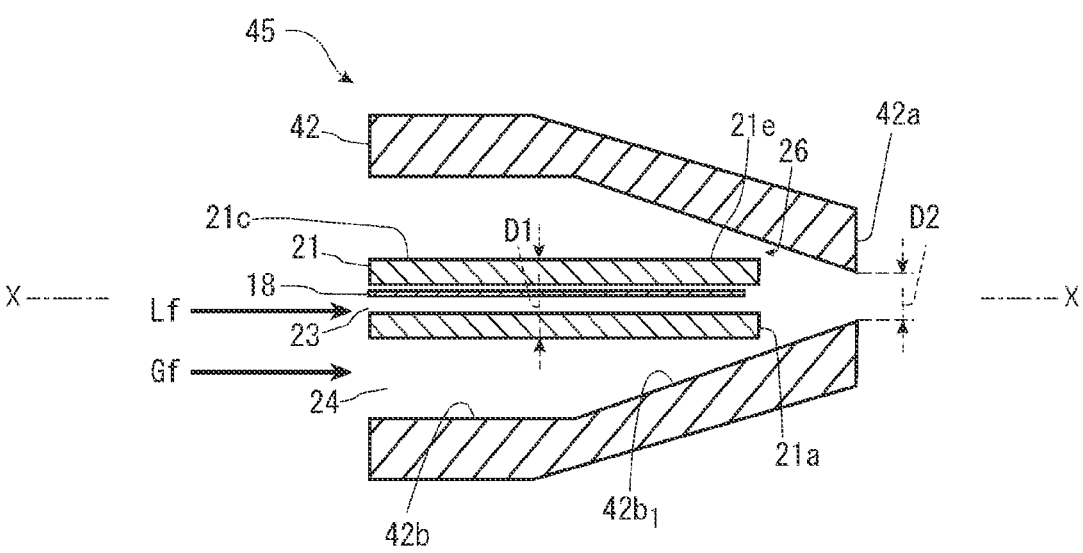
FIGS. 3A and 3B are cross-sectional views illustrating an alternative example of a gas supply tube of the nozzle of the sprayer of the first embodiment of the present invention.
Figure 3B:
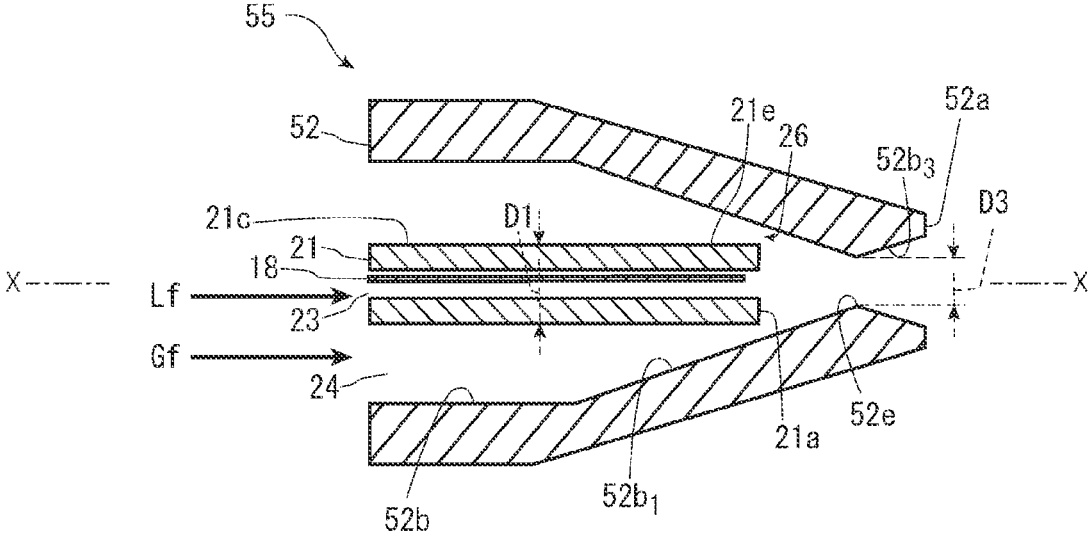

FIGS. 3A and 3B are cross-sectional views illustrating alternative examples of the gas supply tube of the nozzle of the sprayer. Referring to FIG. 3A, the gas supply tube 42 is preferably formed in the nozzle 45 such that at least a portion 42b2 of the inner circumferential surface 42b thereof has a diameter that progressively decreases toward the outlet 42a, and the opening diameter (D2) of the outlet 42a of the gas supply tube 42 is equal to or smaller than the diameter D1 of the outer circumferential surface 21c of the liquid supply tube, at the tip of the outlet 21a of the liquid supply tube 21 than the outlet 21a. Specifically, the formation satisfies a relationship of D1≥D2. As a result, the flow-focus effect is further enhanced, in which the ejected, atomized and electrically charged droplets can flow at a narrower angle than the case of the nozzle 15 illustrated in FIGS. 2A and 2B.

Referring to FIG. 3B, as another alternative example, the gas supply tube 52 is formed in the nozzle 55 such that: a portion 52$b1$ of the inner circumferential surface thereof has a diameter that progressively decreases downstream; the diameter of the inner circumferential surface of the gas supply tube 22 is the smallest at a portion 52$e$, further toward the tip than the outlet 21$a$ of the liquid supply tube 21; and the inner circumferential surface 52$b_3$ has a diameter that progressively increases toward the outlet 52$a$, further toward the tip than the outlet 21$a$ of the liquid supply tube. An opening diameter D3 of a portion 52$e$, at which the diameter of the inner circumferential surface of the gas supply tube 52 is the smallest, is formed to be equal to or smaller than the diameter D1 of the outer circumferential surface 21$c$ of the liquid supply tube 21. Specifically, the formation satisfies a relationship of D1≧D3. As a result, the same flow-focus effect as that of the nozzle 45 of FIG. 3A can be achieved, and the content of the sample liquid Lf becomes more unlikely to adhere to the inner circumferential surface 52$b_3$ having a diameter that progressively increases, and clogging becomes more unlikely to occur even in a case of continuous operation for long hours.

Hereinafter, a variation of the sprayer according to the first embodiment of the present invention will be described. In the variation, configurations different from those of the nozzle 15 illustrated in FIGS. 2A and 2B will be described, and the same reference numerals as those in FIGS. 2A and 2B will be assigned to the same configurations, and descriptions thereof will be omitted. The same configurations omitting description achieve the same effects in the variation, in which description of the effects is omitted for the sake of simplicity.

Figure 4A:
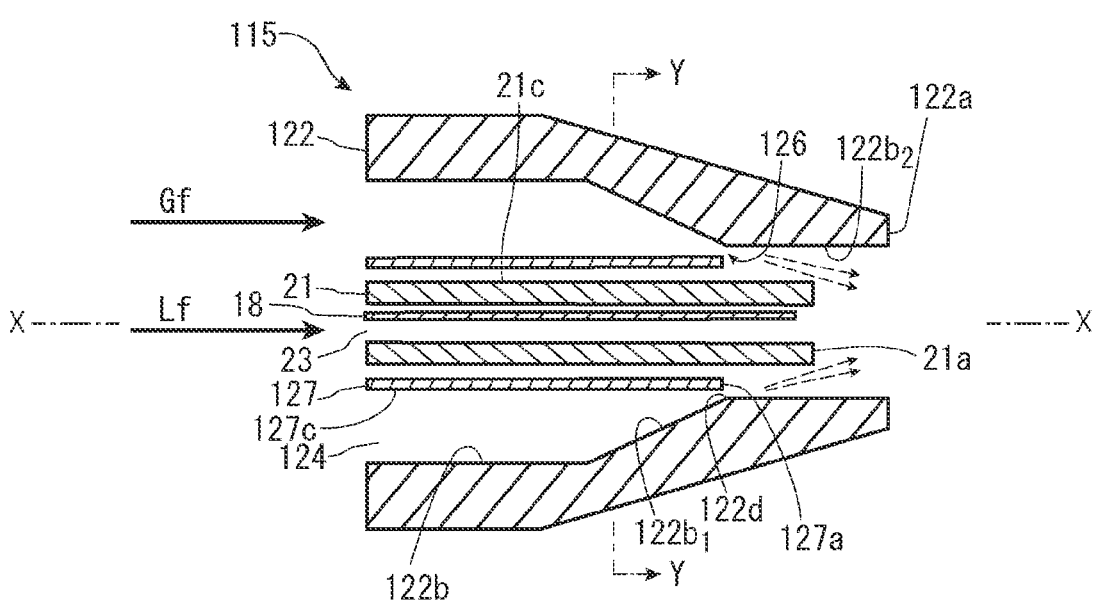
FIGS. 4A and 4B are cross-sectional views of the nozzle of a first variation of the sprayer of the first embodiment of the present invention.
Figure 4B:
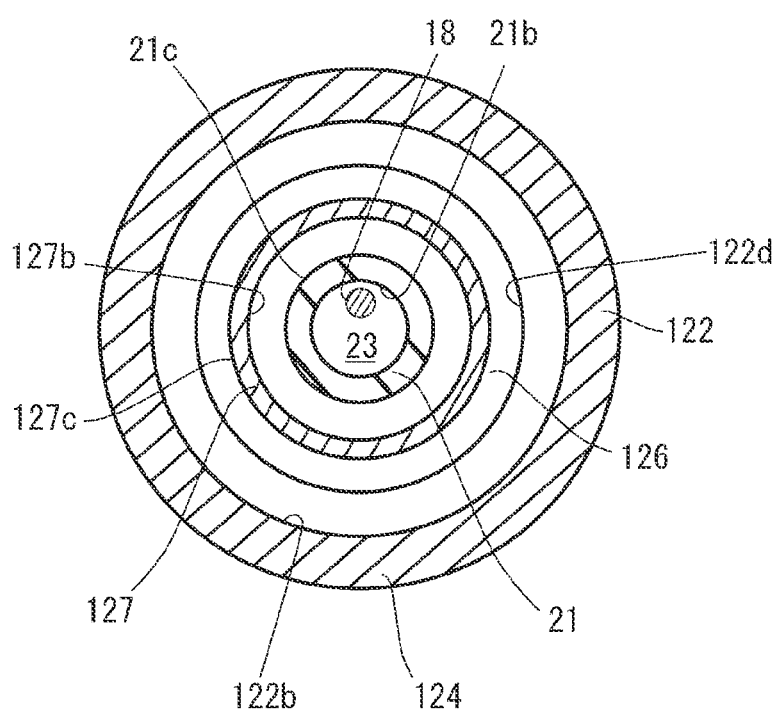

FIG. 4A and FIG. 4B are cross-sectional views of the nozzle of the first variation of the sprayer according to the first embodiment of the present invention, in which FIG. 4A is an enlarged cross-sectional view, and FIG. 4B is a view along arrows Y-Y in FIG. 4A.

Referring to FIGS. 4A and 4B together with FIG. 1, the sprayer of the first variation of the first embodiment includes: the liquid supply tube 21; a gas supply tube 122; a protective tube 127 surrounding the liquid supply tube 21 and provided between the liquid supply tube 21 and the gas supply tube 122; and an electrode 18 for applying high voltage to the sample liquid Lf flowing through the liquid supply tube 21. The electrode 18 has the same configuration as illustrated in FIGS. 2A and 2B. The sprayer has a triple tube structure, in which the tubes are preferably coaxial (central axis X-X) with one another.

The liquid supply tube 21 has the same configuration as the liquid supply tube 21 illustrated in FIGS. 1, 2A and 2B. A second channel 124 of the gas supply tube 122 is a space defined by the outer circumferential surface 127$c$ of the protective tube 127 and the inner circumferential surface 122$b$ of the gas supply tube 122, in which the spraying gas Gf flows through the second channel 124. Note that the spraying gas Gf is not supplied to a space defined by the outer circumferential surface 21$c$ of the liquid supply tube 21 and the inner circumferential surface of the protective tube 127.

In the nozzle 115, a part 122$b_1$ of the inner circumferential face of the gas supply tube 122 is formed so as to progressively decrease in diameter from upstream towards downstream, whereby the channel area of the second channel 124 is formed to gradually narrow.

The tip 127$a$ at the ejection end of the protective tube 127 is located further to the supply end than the outlet 21$a$ of the liquid supply tube 21. In the nozzle 115, a constriction portion 126 of the second channel 124 is formed by the outer circumferential surface 127$c$ of the tip 127$a$ of the protective tube 127 and the portion 122$b_1$ of the inner circumferential surface of the gas supply tube 122. As a result, the second channel 124 is formed such that the channel area of the second channel 124 progressively decreases from the supply end to the constriction portion 126. The spraying gas Gf passes through the constriction portion 126 to gain the flow velocity, and the flow of electrically charged droplets of the sample liquid Lf ejected from the outlet 21$a$ of the liquid supply tube 21 further focuses, promoting atomization of droplets. Furthermore, the droplet ejected from the outlet 21$a$ of the liquid supply tube 21 can be suppressed from flowing back in the second channel 124, and entering the constriction portion 126. As a result, clogging of the constriction portion 126 due to precipitation of components such as salts contained in droplets can be suppressed, whereby stable ejection can be achieved.

The gas supply tube 122 is formed such that the inner circumferential surface 122$b2$ has a constant diameter (inner diameter) from the constriction portion 126 toward the outlet 122$a$. As a result, the flow of the spraying gas Gf ejected from the constriction portion 126 is not blocked by any members, whereby turbulence can be suppressed from being generated. The gas supply tube 122 may be formed such that the inner circumferential surface 122$b2$ of the gas supply tube 122 has a diameter that progressively increases from the constriction portion 126 toward the outlet 122$a$. As a result, the same effects as in the case of the constant diameter can be achieved.

Figure 5A:
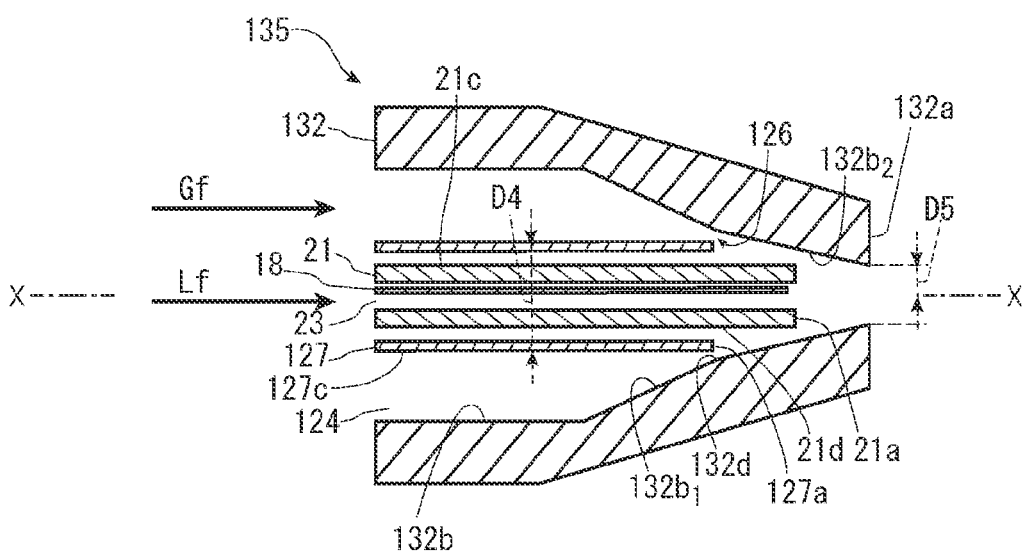
FIGS. 5A and 5B are cross-sectional views of an alternative example of a gas supply tube of the nozzle of the first variation.
Figure 5B:
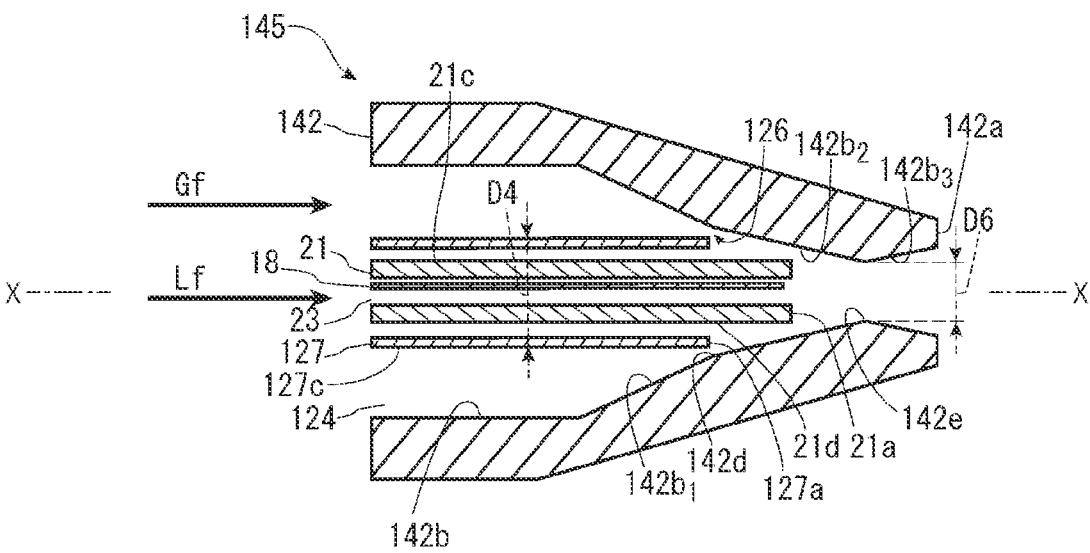

FIGS. 5A and 5B are cross-sectional views of an alternative example of the gas supply tube of the nozzle of the first variation. Referring to FIG. 5A, the gas supply tube 132 is formed in the nozzle 135 such that: at least a portion 132$b_2$ of the inner circumferential surface has a diameter that progressively decreases from the portion 132$d$ of the constriction portion 126 toward an outlet 132$a$; and an opening diameter (D5) of the outlet 132$a$ of the gas supply tube 132 is formed to be equal to or smaller than the diameter D4 of the outer circumferential surface 127$c$ of the protective tube 127, further toward the tip than the outlet 21$a$ of the liquid supply tube 21. Specifically, the formation satisfies a relationship of D4≧D5. As a result, the flow-focus effect can be further enhanced, and the ejected, atomized and electrically charged droplets can form a flow at a narrower angle.

As another alternative example, referring to FIG. 5B, the gas supply tube 142 is formed in the nozzle 145 such that: the portion 142$b2$ of the inner circumferential surface thereof has a diameter that progressively decreases downstream from the portion 142$d$ of the constriction portion 126; the diameter of the inner circumferential surface of the gas supply tube 142 is the smallest at a portion 142$e$, further toward the tip than the outlet 21$a$ of the liquid supply tube; and the inner circumferential surface 142$b3$ has a diameter that progressively increases toward the outlet 142$a$. The opening diameter D6 of the portion 142$e$, at which the diameter of the inner circumferential surface of the gas supply tube 142 is the smallest, is formed to be equal to or smaller than the diameter D4 of the outer circumferential surface 127$c$ of the protective tube 127. Specifically, the formation satisfies a relationship D4≧D6. As a result, the same flow-focus effect as that of the nozzle 135 of FIG. 5A can be achieved, and the content of the sample liquid Lf becomes more unlikely to adhere to the inner circumferential surface $142b_3$, and clogging becomes more unlikely to occur even if an operation is continued for a long time.

In terms of ejecting droplets of the sample liquid Lf in a smaller lateral spreading range with respect to the ejection direction using the flow-focus effect of the flow of the spraying gas Gf, the opening diameter (diameter) of the outlet 21*a* of the liquid supply tube 21 is preferably smaller than the diameter of the outer circumferential surface 127*c* of the tip 127*a* of the protective tube 127 in the constriction portion 126.

Figure 6:
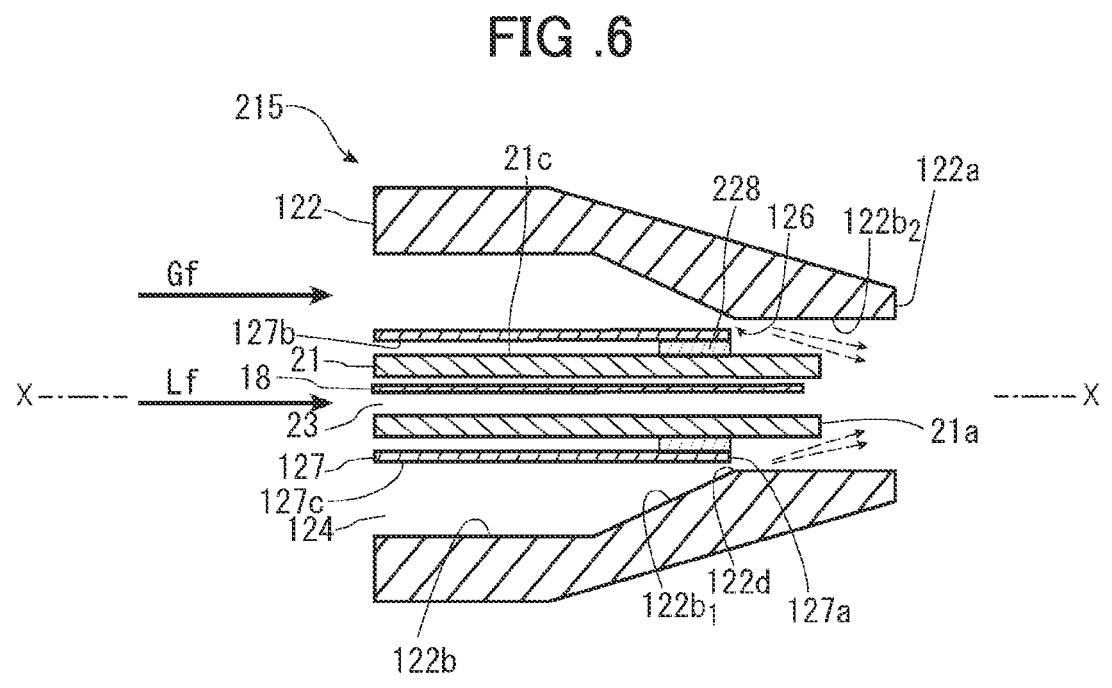

FIG. 6 is an enlarged cross-sectional view of the nozzle of a second variation of the sprayer of the first embodiment of the present invention. Referring to FIG. 6, the nozzle 215 of the second variation includes a blocking member 228 along a circumferential direction in a gap between the outer circumferential surface 21*c* of the liquid supply tube 21 and the inner circumferential surface 127*b* of the protective tube 127, at the tip 127*a* toward the ejection end of the protective tube 127. The gap is blocked by the blocking member 228. Except that the closing member 228 is provided, the nozzle 215 has the same configuration as the nozzle 115 of the sprayer of the first variation illustrated in FIGS. 4A and 4B. With this configuration, the blocking member 228 prevents the spraying gas Gf having passed through the constriction portion 126 from entering the gap between the outer circumferential surface 21*c* of the liquid supply tube 21 and the inner circumferential surface 127*b* of the protective tube 127. As a result, turbulence of the spraying gas Gf is suppressed from occurring, the flow of electrically charged droplets of the sample liquid Lf focuses, and atomization of droplets is promoted. The blocking member 228 may be provided entirely along the axial direction of the gap between the outer circumferential surface 21*c* of the liquid supply tube 21 and the inner circumferential surface 127*b* of the protective tube 127.

SECOND EMBODIMENT

A spray ionization device according to a second embodiment of the present invention has substantially the same configuration as the spray ionization device according to the first embodiment illustrated in FIG. 1, and description of the same elements are omitted.

Figure 7A:
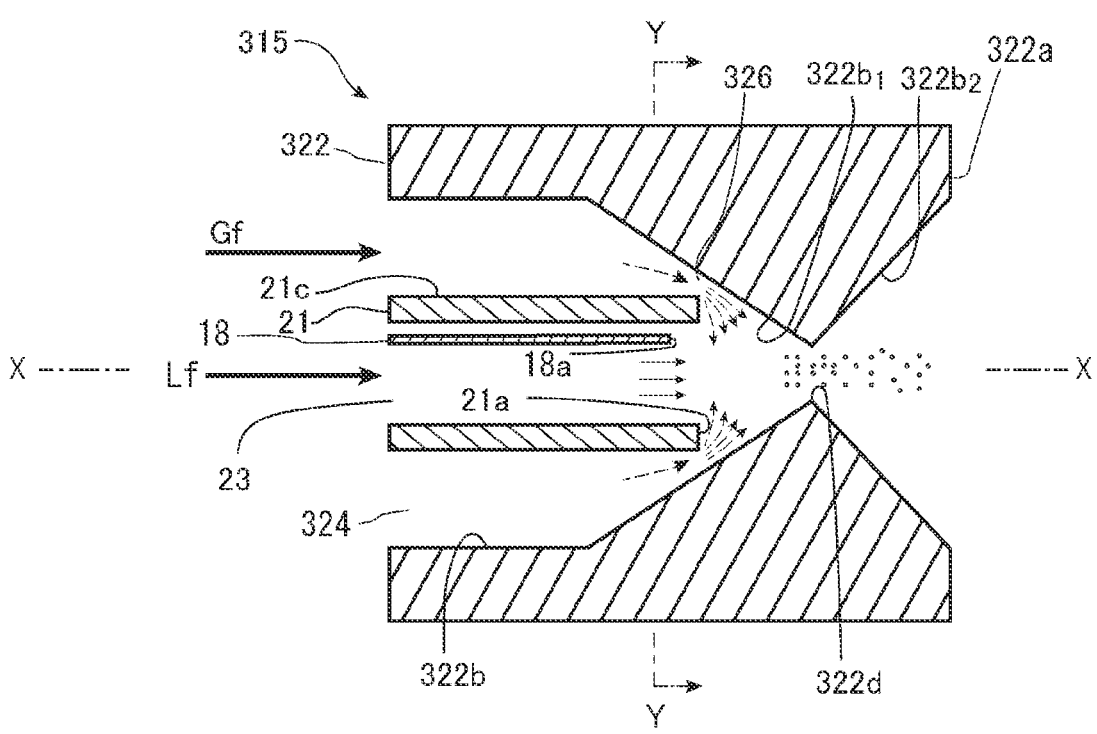
FIGS. 7A and 7B are cross-sectional views of a nozzle of a sprayer of a spray ionization device according to a second embodiment of the present invention.
Figure 7B:
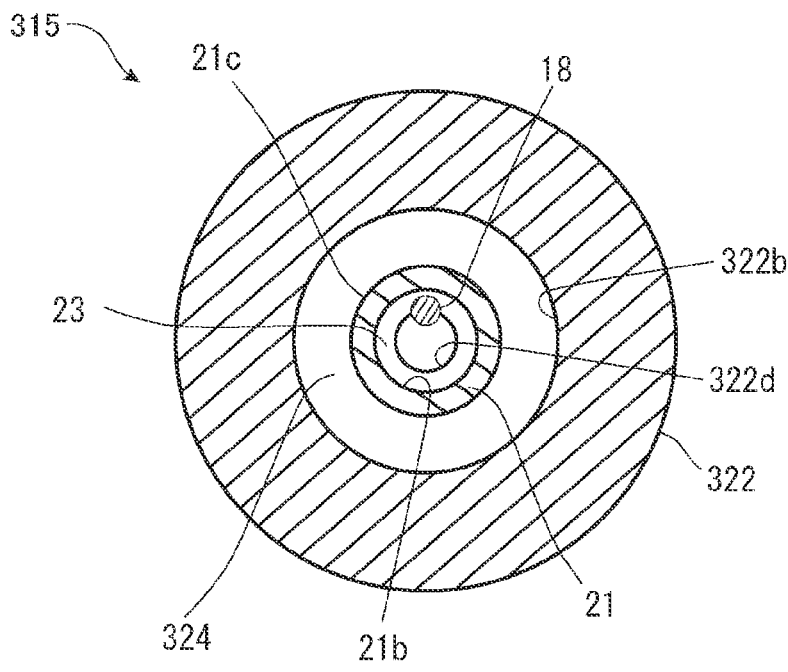

FIGS. 7A and 7B are cross-sectional views of a nozzle of the spray ionization device according to the second embodiment of the present invention, in which FIG. 7A is an enlarged cross-sectional view of the nozzle, and FIG. 7B is a view along arrows Y-Y shown in FIG. 7A.

Referring to FIGS. 7A and 7B together with FIG. 1, the sprayer of the spray ionization device according to the second embodiment of the present invention includes: a liquid supply tube 21; a gas supply tube 322; and an electrode 18 for applying high voltage to a sample liquid Lf flowing through the liquid supply tube 21. The sprayer has a double tube structure, in which the tubes are preferably coaxial (central axis X-X) with one another. The liquid supply tube 21 has substantially the same configuration as the liquid supply tube 21 of the first embodiment illustrated in FIGS. 1, 2A and 2B. The liquid supply tube 21 includes a first channel 23 defined by the inner circumferential surface of the liquid supply tube 21 and extending in the axial direction. The sample liquid Lf flows through the liquid supply tube 21 and is ejected from an outlet 21*a*. The gas supply tube 322 has substantially the same configuration as the gas supply tube 22 illustrated in FIGS. 1, 2A and 2B.

The gas supply tube 322 includes a second channel 324 defined by the inner circumferential surface 322*b* of the gas supply tube 322 and the outer circumferential surface 21*c* of the liquid supply tube 21 and extending in the axial direction. The spraying gas Gfs flows through the second channel 324. The electrode 18 extends from the supply side to the first channel 23 within the liquid supply tube 21 so that the leading end 18*a* is the same position as the outlet 21*a* of the liquid supply tube 21 or further towards the supply side than the outlet 21*a*, and is similar to the configuration shown in FIGS. 1, 2A and 2B.

In the nozzle 315, the outlet 21*a* of the liquid supply tube 21 of the sprayer is located further toward the supply end than the outlet 322*a* of the gas supply tube 322. The gas supply tube 322 includes an ejection port 322*d* between the outlet 322*a* of the gas supply tube 322 and the outlet 21*a* of the liquid supply tube 21. The ejection port 322*d* is a portion in which the diameter of the inner circumferential surface of the gas supply tube 322 is the smallest, and the ejection port 322*d* is formed narrower than the opening of the outlet 21*a* of the liquid supply tube 21. For example, the opening diameter of the ejection port 322*d* is smaller than the opening diameter of the outlet 21*a* of the liquid supply tube 21. With this configuration, the charged sample liquid Lf ejected from the outlet 21*a* of the liquid supply tube 21 collides with the spraying gas Gf having flowed through the second channel 324, at high speed in the region between the outlet 21*a* and the ejection port 322*d*, whereby the electrically charged droplets of the sample liquid Lf are atomized and ejected from the outlet 322*a* through the ejection port 322*d*.

In the nozzle 315, the second channel 324 preferably includes a constriction portion 326 in which the channel area of the second channel 324 is the smallest. The constriction portion 326 is formed by a gap between a portion 322*b*1, in which the inner circumferential surface 322*b* of the gas supply tube 322 has a diameter that progressively decreases from upstream to downstream, and the outer circumferential surface 21*c* of the outlet 21*a* of the liquid supply tube 21. The spraying gas Gf gains linear velocity in the constriction portion 326 and collides with the sample liquid Lf at high speed in the region between the outlet 21*a* of the liquid supply tube 21 and the ejection port 322*d*, whereby atomization of electrically charged droplets of the sample liquid Lf is promoted. The spraying gas Gf is ejected from the constriction portion 326 at high speed; therefore, the content of the sample liquid Lf is unlikely to adhere to the vicinity of the ejection port 322*d*, and clogging is unlikely to occur. The liquid supply tube 21 is supported in a cantilever manner at the supply end, whereby when the spraying gas Gf is ejected from the constriction portion 326 at high speed, the outlet 21*a* of the liquid supply tube 21 easily vibrates in a direction perpendicular to the ejection direction. Then, the gap at the constriction portion 326 temporally changes, so that the flow rate of the spraying gas Gf having passed through the constriction portion 326 changes, and the spraying gas flows locally at higher speed. As a result, the content of the sample liquid Lf is further unlikely to adhere to the vicinity of the ejection port 322*d*, and clogging is further unlikely to occur.

Hereinafter, a variation of the sprayer according to the second embodiment of the present invention will be described. In the variation, configurations different from the nozzle 315 illustrated in FIGS. 7A and 7B will be described, the same reference numerals as in FIGS. 7A and 7B or FIGS. 2A and 2B will be assigned to the same configurations, and description thereof will be omitted. The same configurations omitting description achieve the same effects in the variation, in which description of the effects is omitted for the sake of simplicity.

Figure 8A:
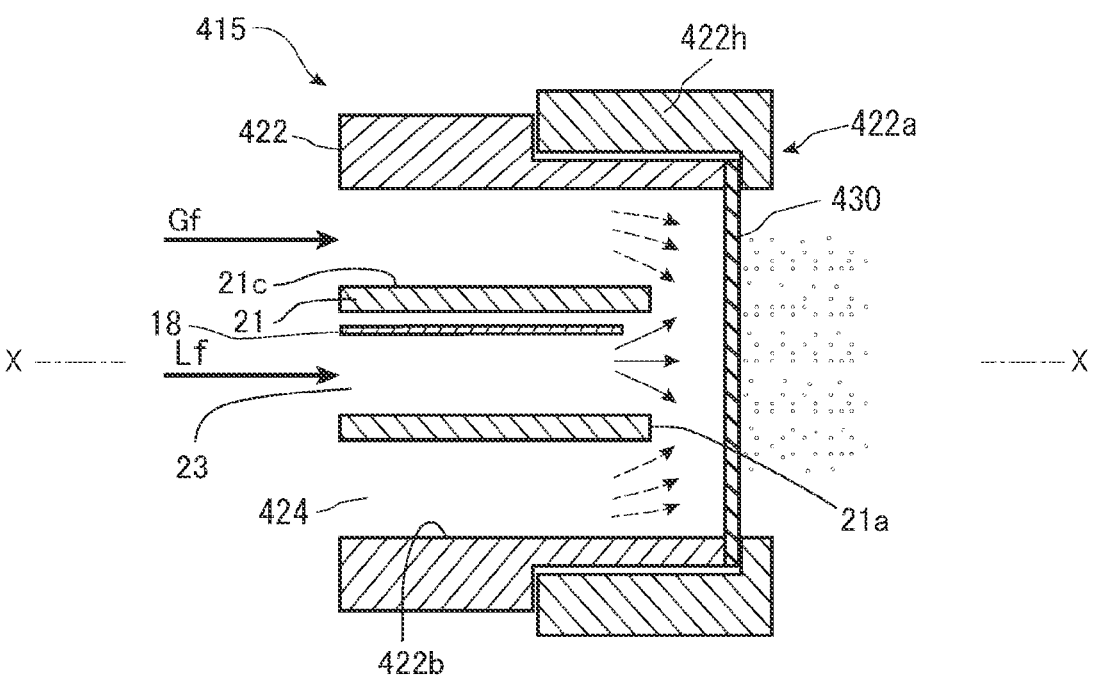
FIGS. 8A and 8B are views illustrating a nozzle of the first variation of the sprayer according to the second embodiment of the present invention.
Figure 8B:
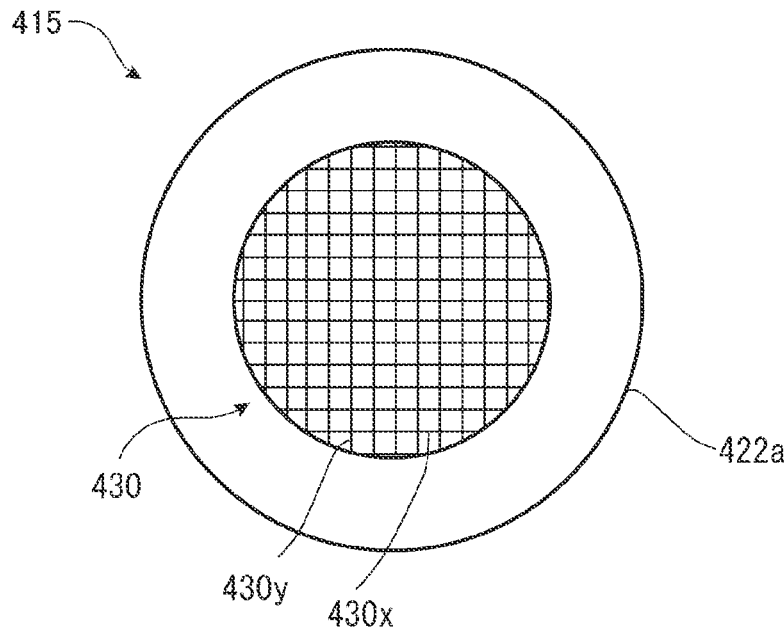

FIGS. 8A and 8B are views illustrating a nozzle of a first variation of the sprayer according to the second embodiment of the present invention, in which FIG. 8A is an enlarged cross-sectional view, and FIG. 8B is a view of the nozzle from the ejection end.

Referring to FIGS. 8A and 8B together with FIG. 1, the sprayer of the first variation of the second embodiment includes a liquid supply tube 21, a gas supply tube 422, and an electrode 18 for applying high voltage to the sample liquid Lf flowing through the liquid supply tube 21. The electrode 18 has the same configuration as illustrated in FIGS. 1, 2A and 2B. The sprayer has a double tube structure, in which the tubes are preferably coaxial (central axis X-X) with one another.

The liquid supply tube 21 has the same configuration as the liquid supply tube 21 of the second embodiment illustrated in FIGS. 7A and 7B, and the sample liquid Lf is ejected from the outlet 21a in the nozzle 415.

The gas supply tube 422 includes a second channel 424 defined by the inner circumferential surface 422b of the gas supply tube 422 and the outer circumferential surface 21c of the liquid supply tube 21 and extending in the axial direction. The spraying gas Gf flows through the second channel 424 and is ejected from the outlet 422a in the nozzle 415.

In the nozzle 415, a reticulated member 430 is provided to the outlet 422a of the gas supply tube 422. The reticulated member 430 is retained by a retaining member 422h and arranged so as to cover the opening of the outlet 422a of the gas supply tube 422. For example, a sheet-like mesh sheet can be used for the reticulated member 430. A dielectric material can be used for the mesh sheet, and for example, nylon fiber can be used.

The reticulated member 430 has horizontal lines 430x and vertical lines 430y with an interval of 70 μm, for example, in which a vertical and horizontal size of each aperture is 35 μm, for example. The distance between the outlet 21a of the liquid supply tube 21 and the reticulated member 430 is set to 100 μm, for example, and is preferably set to 5 μm to 300 μm.

With this configuration, electrically charged droplets of the sample liquid Lf ejected from the outlet 21a of the liquid supply tube 21 together with the spraying gas Gf having flowed through the second channel 424 collides with the reticulated member 430 at high speed, whereby the electrically charged droplets of the sample liquid Lf are atomized in the region between the outlet 21a and the reticulated member 430, and ejected through the opening of the reticulated member 430 by way of the spraying gas Gf.

Figure 9:
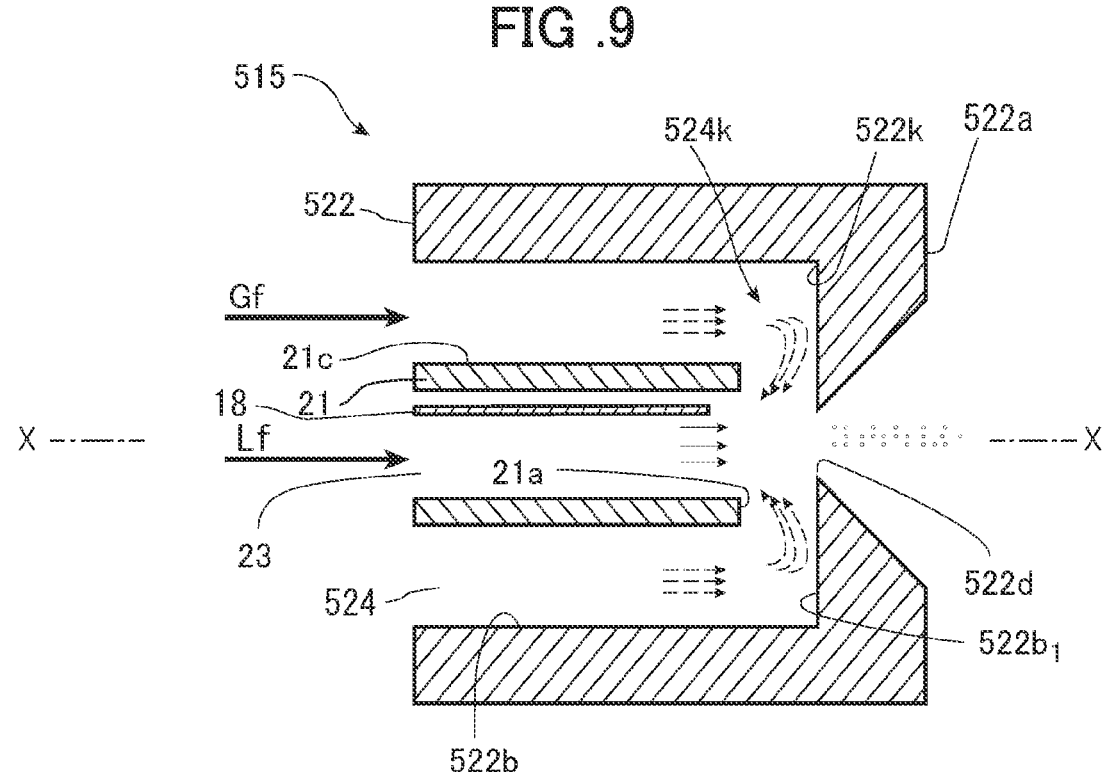
FIG. 9 is a cross-sectional view of the second variation of the nozzle of the sprayer of the second embodiment of the present invention.

FIG. 9 is an enlarged cross-sectional view of a nozzle of a second variation of the sprayer of the second embodiment of the present invention. Referring to FIG. 9 together with FIG. 1, the second variation of the sprayer of the second embodiment includes a liquid supply tube 21, a gas supply tube 522, and an electrode 18 for applying high voltage to the sample liquid Lf flowing through the liquid supply tube 21. The electrode 18 has the same configuration as illustrated in FIGS. 1, 2A and 2B. The sprayer has a double tube structure, in which the tubes are preferably coaxial (central axis X-X) with one another.

The liquid supply tube 21 has the same configuration as the liquid supply tube 21 of the second embodiment illustrated in FIGS. 7A and 7B, and the sample liquid Lf is ejected from the outlet 21a in the nozzle 515. The gas supply tube 522 includes a second channel 524 defined by the inner circumferential surface 522b of the gas supply tube 522 and the outer circumferential surface 21c of the liquid supply tube 21 and extending in the axial direction. The spraying gas Gf flows through the second channel 524 and is ejected from the outlet 522a in the nozzle 415.

In the nozzle 515, the inner circumferential surface 522b of the gas supply tube 522 has a diameter that decreases at a portion 522k further toward the tip than the outlet 21a of the liquid supply tube 21, and the inner circumferential surface 522b1 is bent perpendicularly to the X-axis direction. A bent portion 524k bent toward the outlet 21a of the liquid supply tube 21 is formed in the second channel 524. As a result, the spraying gas Gf flows toward the outlet 21a of the liquid supply tube 21 at the bent portion 524k, and collides with the sample liquid Lf at high speed in the region between the outlet 21a and an ejection port 522d, whereby the electrically charged droplets of the sample liquid Lf are atomized.

The inner circumferential surface 522b1 of the gas supply tube 522 is bent perpendicularly to the X-axis direction, or may be bent at an angle that is larger or smaller than the vertical angle, depending on the flow velocity or the like of the spraying gas Gf. The spraying gas Gf enters the inside of the liquid supply tube 21 from the outlet 21a and collides with the electrically charged droplets of the sample liquid Lf, whereby atomization of the electrically charged droplets of the sample liquid Lf is promoted.

The ejection port 522d may be provided with the reticulated member 430 of the sprayer of the first variation illustrated in FIGS. 8A and 8B. As a result, atomization of electrically charged droplets of the sample liquid Lf is further promoted.

As a further variation of the sprayer of the spray ionization device according to the second embodiment of the present invention, a second gas supply tube may be provided so as to surround the gas supply tube with a gap.

Figure 10:
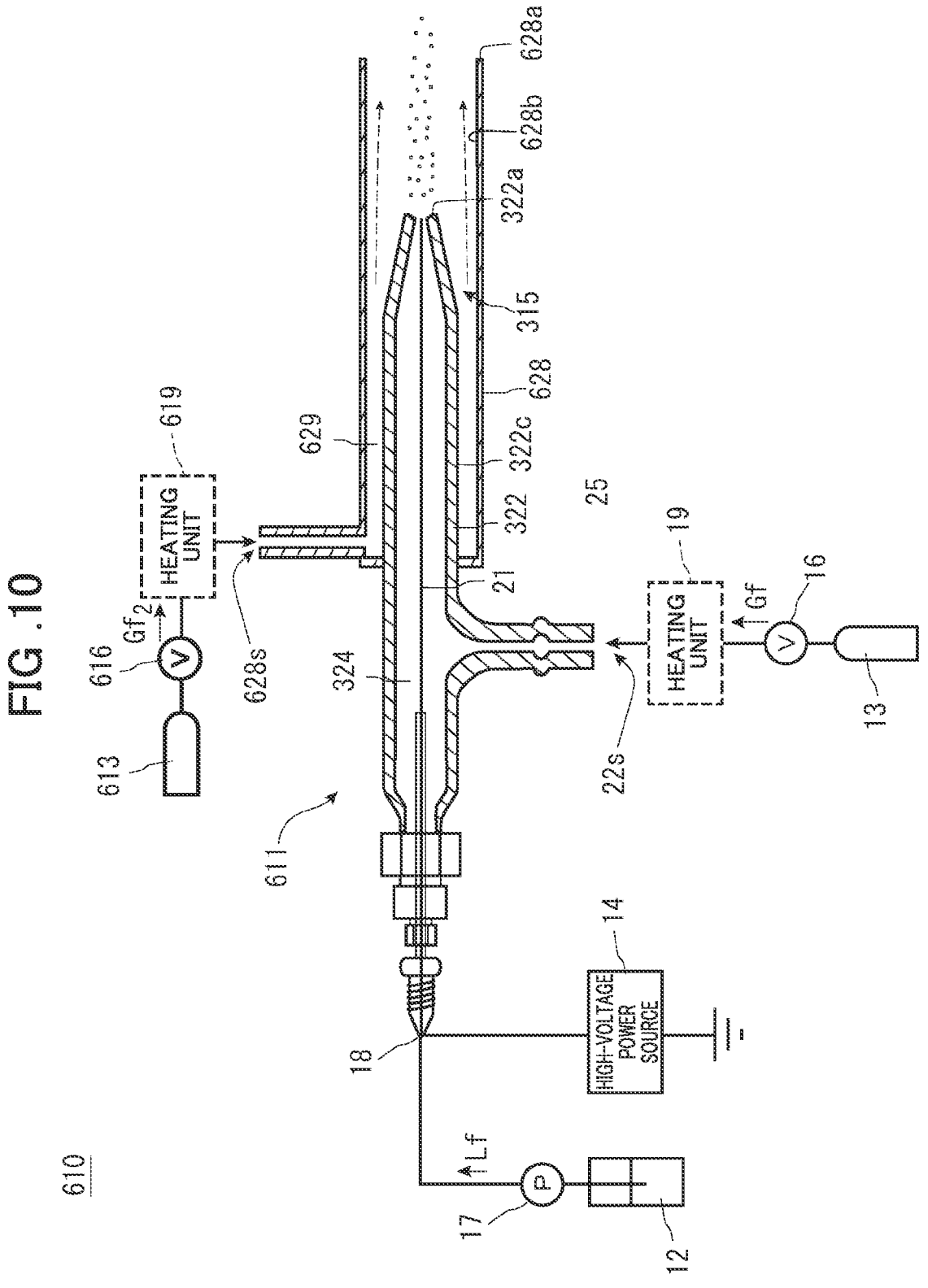
FIG. 10 is a diagram schematically illustrating a configuration of another variation of the spray ionization device according to the second embodiment of the present invention.

FIG. 10 is a diagram schematically illustrating a configuration of another variation of the spray ionization device according to the second embodiment of the present invention. Referring to FIG. 10, a spray ionization device 610 includes a second gas supply tube 628 in which a sprayer 611 surrounds a gas supply tube 322, and the nozzle 315 is the nozzle 315 illustrated in FIGS. 7A and 7B. In the second gas supply tube 628, a cylinder 613 supplies sheath gas Gf₂ via a valve 616 to a supply port 628s of.

The second gas supply tube 628 includes a third channel 629 defined by an outer circumferential surface 322c of the gas supply tube 322 and an inner circumferential surface 628b of the second gas supply tube 628 and extending in the axial direction. The inner circumferential surface 628b of the second gas supply tube 628 is formed so as to have a constant diameter toward an outlet 628a. The flow of sheath gas Gf₂ flowing through the third channel 629 is restricted from spreading by the inner circumferential surface 628b of the second gas supply tube 628 toward the outlet 628a, and the atomized and electrically charged droplets ejected from the nozzle 315 are enveloped in the sheath gas Gf₂. As a result, the outlet 628a of the second gas supply tube 628 ejects the focused, atomized and electrically charged droplets along the axis in the ejection direction. With this configuration, even if the nozzle 315 cannot eject atomized droplets with sufficient focusing thereof, the sprayer 611 can eject focused and atomized droplets.

A heating unit 619 may be provided downstream of the valve 616 so as to supply the sheath gas Gf₂ as heated gas; or a heating unit such as a ring heater (not illustrated) may be provided downstream of the outlet 322a of the gas supply tube 322 so as to surround a second gas supply tube 628. As a result, desolvation of droplets can be supported.

The sprayer 611 can employ the nozzle 415 illustrated in FIGS. 8A and 8B or the nozzle 515 illustrated in FIG. 9, whereby the same effects as the nozzle 315 can be achieved.

The sprayer 611 may employ the nozzle 15 illustrated in FIGS. 2A and 2B, the nozzle 45 or 55 illustrated in FIGS. 3A and 3B, the nozzle 115 illustrated in FIGS. 4A and 4B, the nozzle 135 or 145 illustrated in FIGS. 5A and 5B, or the nozzle 215 illustrated FIG. 6 of the first embodiment.

Figure 11:
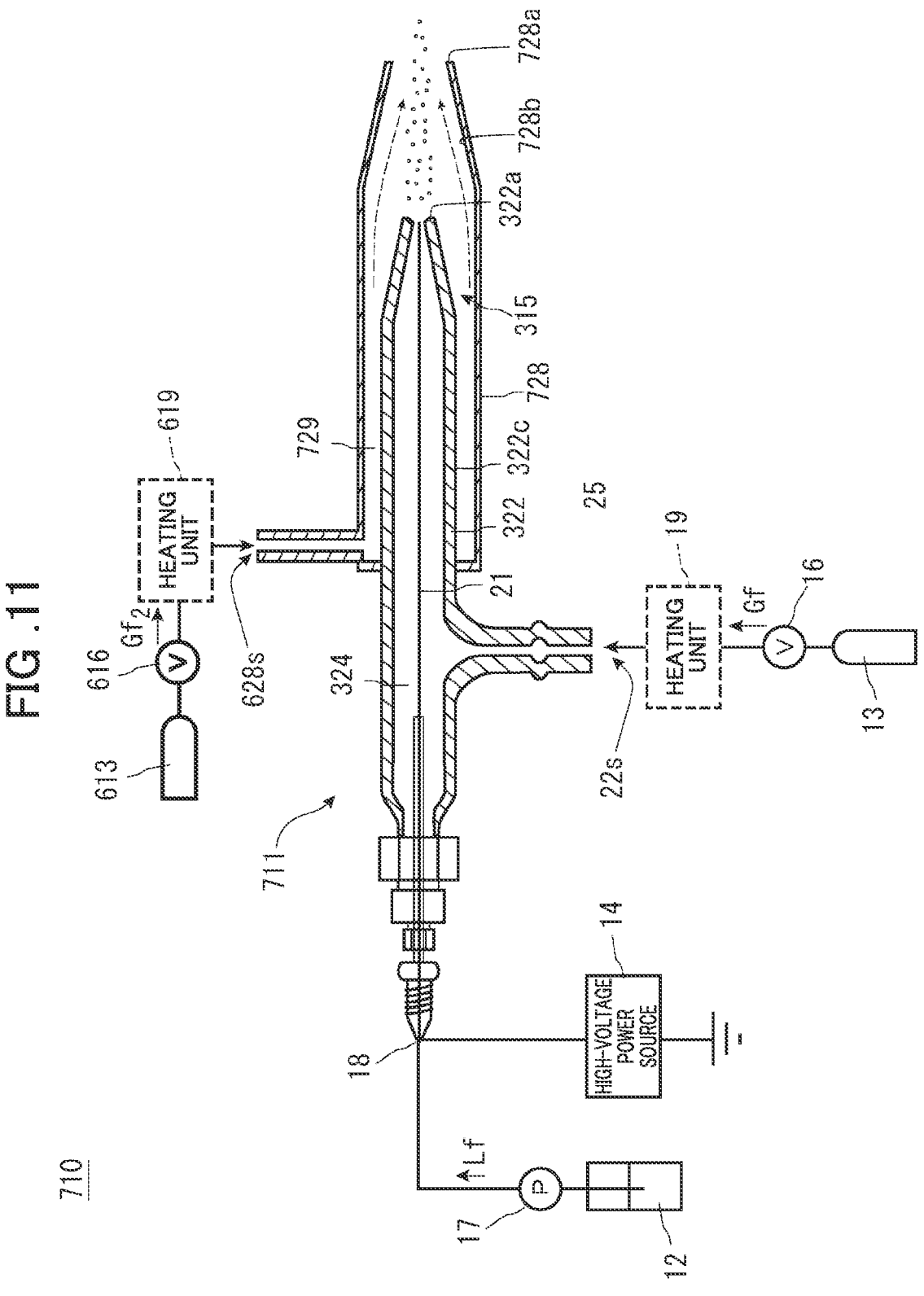
FIG. 11 is a diagram schematically illustrating a configuration of an alternative example of a second gas supply tube of still another variation of the spray ionization device according to the second embodiment of the present invention.

FIG. 11 is a diagram schematically illustrating a configuration of the alternative example of the second gas supply tube of another variation of the spray ionization device. Referring to FIG. 11, a second gas supply tube 728 of a sprayer 711 of a spray ionization device 710 has the same configuration as the second gas supply tube 628, except that the tip shape of the second gas supply tube 728 differs from the tip shape of the second gas supply tube 628 illustrated in FIG. 10. An inner circumferential surface 728b of the second gas supply tube 728 is formed to have a diameter that progressively decreases toward an outlet 728a, and the channel area of a third channel 729 progressively decreases accordingly.

The sheath gas $Gf_2$ flowing through the third channel 729 flows toward the outlet 728a such that the flow focuses while being restricted by the inner circumferential surface 728b of the second gas supply tube 728. The atomized and electrically charged droplets ejected from the nozzle 315 are enveloped in the sheath gas $Gf_2$ and focus onto the axial center along the ejection direction, and the focused, atomized and electrically charged droplets are ejected from the outlet 728a of the second gas supply tube 728. With this configuration, even if the nozzle 315 cannot eject atomized droplets with sufficient focusing thereof, the sprayer 711 can eject focused and atomized droplets.

Hereinafter, measurement examples prepared using examples of a spray ionization device according to embodiments of the present invention will be shown. The Examples used a configuration in which the sprayer 611 has the nozzle 135 shown in FIG. 5A in the spray ionization device 610 of a first variant of the second embodiment, shown in FIG. 10. Tungsten (W) wire of 50 μm diameter was used in the electrode 18, and provided from a supply side to outlet in the liquid supply tube. It should be noted that the W wire was arranged so as not to project from the outlet. The inside diameter of the liquid supply tube was 110 μm, and the outlet diameter of the liquid supply tube was 200 μm. A reference example defined a case of not applying voltage to the electrode 18 in the Examples. In the Examples and Reference Example, heating of the sprayed droplets was performed by heating the sheath gas.

The spray ionization device of the Comparative Example was an ESI ion source applying the gas spray assist electrospray ionization (ESI) method, and used a sprayer (ESI probe (ion source)) belonging to a mass spectrometer model LCMS-8060 manufactured by Shimadzu Corp. The ESI probe of the Comparative Example has a triple-tube structure, and includes a liquid supply tube, a first gas supply tube surrounding the liquid supply tube and circulating the spraying gas, and a second gas supply tube surrounding the first gas supply tube, and circulating heated gas. The ejection port of the liquid supply tube is provided further downstream than the ejection port of the spraying gas of the first gas supply tube and the ejection port of the heated gas of the second gas supply tube. The liquid supply tube and first gas supply tube are formed with a metal material (SUS316).

Using the first gas supply tube as an electrode, a high-voltage power source was connected to this.

The spray ionization devices of the Examples, Reference Example and Comparative Example were applied to the LC (liquid chromatography)/MS (mass spectrometry)/MS device, a model LC-30 series manufactured by Shimadzu Corp. was used as the LC device, and the model LCMS-8060 manufactured by Shimadzu Corp. was used as the MS/MS device. At the interface between the LC device and MS/MS device, it sprays towards the ion capture port of the MS/MS device, and heating of sprayed droplets was performed by heating the sheath gas. The heating of sprayed droplets in the Comparative Example was performed by heating the interface space. It should be noted that, in the Comparative Example, the interface space became 60° C., even in a case without this heating. The heating of these sprayed droplets is called simply heat treatment hereinafter.

In the Examples and Comparative Example, the high-voltage power supply (model HCZE-30PN0.25 manufactured by Matsusada Precision Inc.) was connected to the electrode, and direct current voltage was applied to the sample liquid at the ion capture port of the MS/MS device.

Measurement Example 1: Detection of Reserpine

A reserpine solution having a concentration of 1 ppb was introduced in an amount of 1 μL from the injector of the LC device, a 70% acetonitrile aqueous solution with mobile phase: acetonitrile=3:7 was fed at 400 μL/min as eluent using the LC device, multiple-reaction monitoring (MRM) analysis was performed by the MS/MS device by ejecting by the spray ionization devices of the Examples, Reference Example and Comparative Example, and the total area of the peak of the ion signal in the positive ion mode with mass-to-charge ratio m/z=609.3>195.0 was measured, for a specific product ion produced by destroying precursor ion.

Using nitrogen gas as the spraying gas, a flowrate of 1.25 L/min was established for the Examples and Reference Example, and the flowrate of 2.5 L/min was established for the Comparative Example.

Figure 12A:
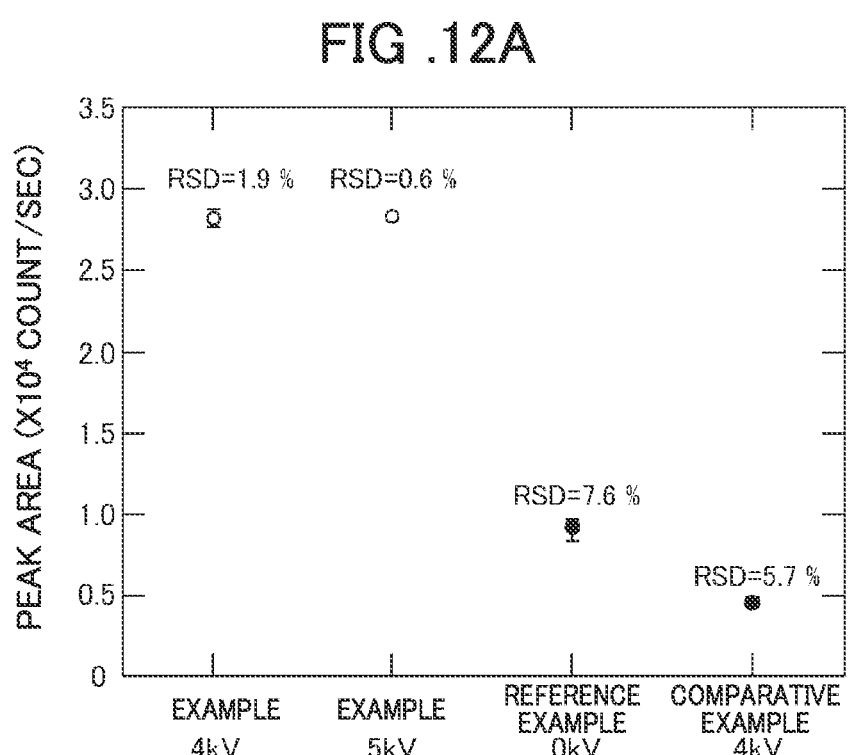
FIGS. 12A and 12B are graphs illustrating a Measurement Example of reserpine.
Figure 12B:
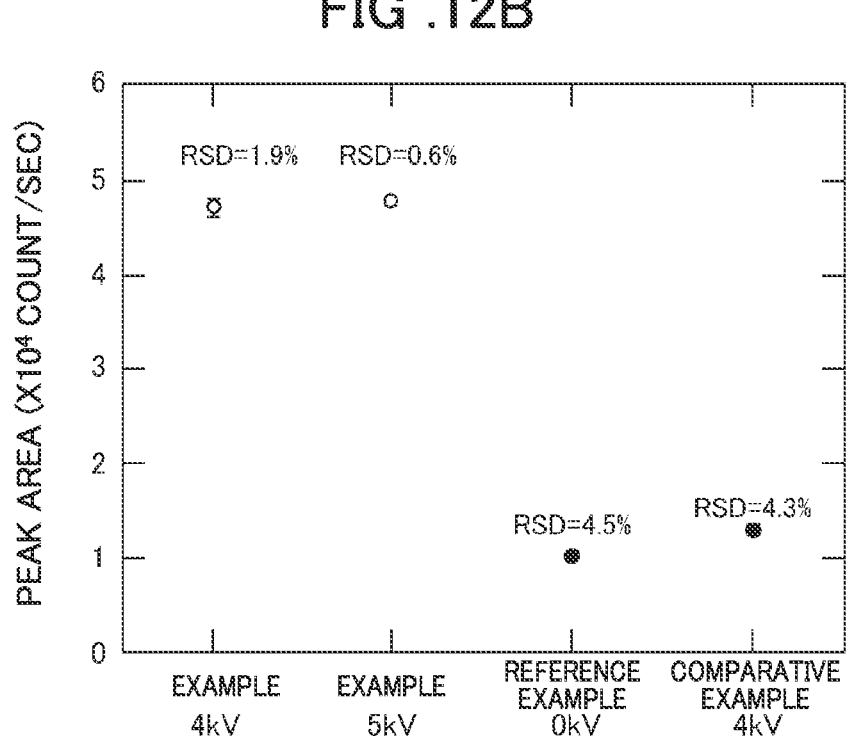

FIGS. 12A and 12B are graphs showing the measurement example of reserpine, with FIG. 12A being a case of not performing heat treatment, and FIG. 12B being a case of performing heat treatment at 60° C. in the Examples and Reference Example, and at 100° C. in the Comparative Example. The vertical axis is the peak area (count number), and by counting for 197 milliseconds per one measurement and measuring four times, the average value, standard deviation and relative standard device (RSD) (%) (=average value/standard deviation×100) were calculated, and the average value is shown by circles and the standard deviation is shown by error bars.

Referring to FIG. 12A, the Examples were $2.8 \times 10^4$ counts at applications of +4 kV and +5 kV; whereas, the Reference Example was a $0.9 \times 10^4$ count without voltage application, and the Comparative Example was $0.45 \times 10^4$ at application of +4 kV. In the Examples, 6 times the signal intensity was obtained in the case of no heat treatment relative to Comparative Example, whereby it was found that the Examples much more efficiently ionized than the Comparative Example. In addition, in the Examples, 3 times the signal intensity was obtained relative to the case without voltage application of the Reference Example, whereby it was found to be more efficiently ionized by voltage application.

Referring to FIG. 12B, the Examples were $4.7 \times 10^4$ counts at the application of +4 kV, and $4.8 \times 10^4$ counts at the application of +5 kV; whereas, the Reference Example was 1.0×10$^4$ counts without voltage application, and the Comparative Example was 1.3×10$^4$ counts with the application of +5 kV. In the Examples, 3.6 times the signal intensity was obtained in the case of there being heat treatment relative to the Comparative Example, whereby it was found that the Examples much more efficiently ionized reserpine than the Comparative Example. In addition, in the Examples, 4.6 times the signal intensity was obtained relative to the case of no voltage application of the Reference Example, whereby it was found to efficiently ionize reserpine by voltage application.

The Examples had smaller relative standard deviation (RSD) than the Reference Example and Comparative Example, either without heat treatment or with heat treatment, and from this matter it is found that the spray ionization device of the Examples was able to ionize reserpine much more stably than the Reference Example and Comparative Example.

Measurement Example 2: Detection of Chloramphenicol

A concentration of 10 ppb chloramphenicol was introduced in an amount of 1 μL from the injector of the LC device, a 70% acetonitrile aqueous solution prepared with mobile phase: acetonitrile=3:7 was delivered at 400 μL/min using the LC device as eluate, was sprayed by the spray ionization devices of the Examples, Reference Example and Comparative Example, MRM analysis was performed by the MS/MS device similarly to Measurement Example 1, and the total area of the peak of the ion signal was measured in the negative ion mode of mass-to-charge ratio m/z=321.00>152.10.

Using nitrogen gas as the spraying gas, the flowrate was set to 1.25 L/min in the Examples and the Reference Example, and set to 1.5 L/min in the Comparative Example.

Figures 13A, 13B:
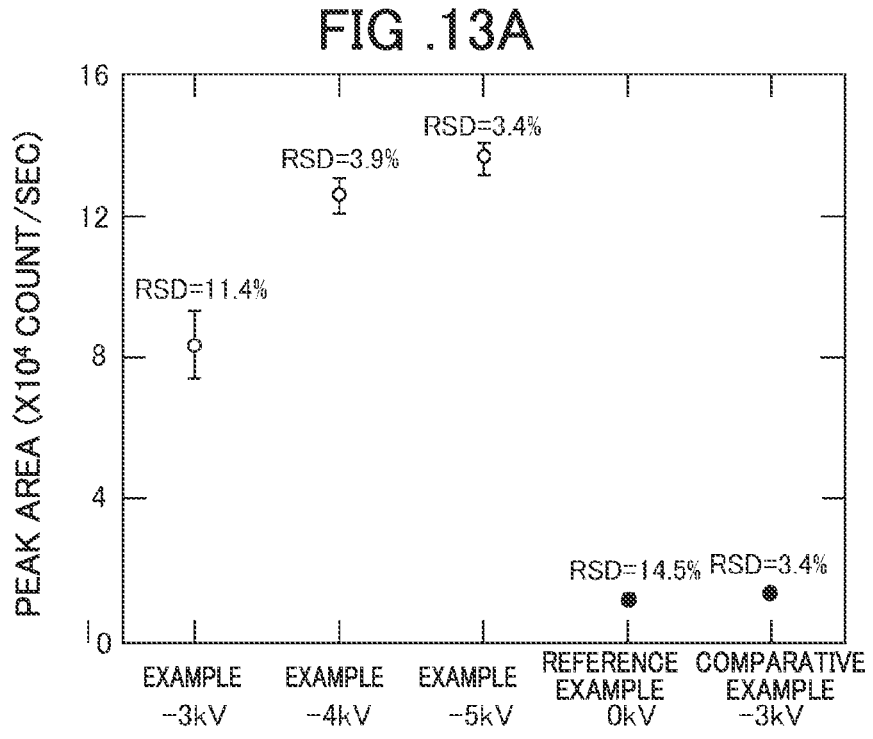
FIGS. 13A and 13B are graphs illustrating a Measurement Example of chloramphenicol.

FIGS. 13A and 13B are graphs illustrating a Measurement Example of chloramphenicol, with FIG. 13A being a case of not performing heat treatment, and FIG. 13B being a case of performing heat treatment at 60° C. in the Examples and Reference Example, and at 100° C. in the Comparative Examples. In FIGS. 13A and 13B, the vertical axis is the peak area (count number), and shows the average value, standard deviation and RSD, similarly to Measurement Example 1.

Referring to FIG. 13A, the Examples were 8.3×10$^4$ counts to 13.6×10$^4$ counts with application of −3 kV to −5 kV; whereas, the Reference Example was 1.1×10$^4$ counts without voltage application, and the Comparative Example was 1.3×10$^4$ counts with application of −3 kV. In the Examples, 6.2 times the signal intensity was obtained in the case of applying −3 kV and no heat treatment relative to the Comparative Example, whereby it was found that the Examples could much more efficiently ionize than the Comparative Example. In addition, in the Example, 7.4 times the signal intensity was obtained at application of −3 kV relative to a case of no voltage application in the Reference Example, whereby it was found it could be more efficiently ionized by voltage application.

Referring to FIG. 13B, the Examples were 11.0×10$^4$ counts to 19.4×10$^4$ counts with application of −3 kV to −5 kV; whereas, it was 1.6×10$^4$ counts without voltage application in the Reference Example, and the Comparative Example was 2.0×10$^4$ counts with application of −3 kV. In the Examples, 5.4 times the signal intensity was observed in the case with application of −3 kV and heat treatment relative to the Comparative Example, whereby it was found that the Example could ionize chloramphenicol much more efficiently than the Comparative Example. In the Examples, 6.7 times the signal intensity was obtained with the application of −3 kV relative to the case without voltage application in the Relative Example, whereby it was found that chloramphenicol could be ionized more efficiently by voltage application.

In the foregoing, the preferred embodiments of the present invention have been described in detail; however, the present invention is not limited to the specific embodiments, and various modifications and changes can be made within the scope of the present invention described in the claims.

The shape of the cross-section and the channel of the liquid supply tube has been described as circular, but may be triangular, square, pentagonal, hexagonal or other polygonal shapes, or other shapes such as an elliptical shape. The shape of the outer circumferential surface and the inner circumferential surface of the gas supply tube and the second gas supply tube can be selected from these shapes, depending on the shape of the liquid supply tube.

The spray ionization device of each of the aforementioned embodiments can be used as an ion source of various devices; for example, in the field of trace sample analysis, the spray ionization device can be used for mass spectrometry such as mass spectrometry of molecules in a biological sample, elemental analysis, chemical morphology analysis, and charged particle analysis.

In the field of surface treatment, the spray ionization device of each of the aforementioned embodiments can be used in surface coating techniques of spraying electrically charged droplets, and in the field of granulation, can be used in particle forming techniques by spraying electrically charged droplets of suspension.

In the field of food production, healthcare, and agriculture, the spray ionization device of each of the aforementioned embodiments can be used in space processing utilizing sterilization, deodorization, dust collection, and chemical reactions, utilizing gas-phase or spatial chemical reactions by spraying electrically charged droplets.

EXPLANATION OF REFERENCE NUMERALS

10, 610, 710: spray ionization device
11, 611, 711: sprayer
14: high-voltage power source
15, 45, 55, 115, 135, 145, 215, 315, 415, 515: nozzle
18: electrode
19, 619: heating unit
21: liquid supply tube
22, 42, 52, 122, 132, 142, 322, 422, 522: gas supply tube
23: first channel
24, 124, 324, 424, 524: second channel
26, 126, 326: constriction portion
127: protective tube
430: reticulated member
628, 728: second gas supply tube
629, 729: third channel
Lf: sample liquid
Gf: spraying gas
Gf$_2$: sheath gas
The invention claimed is:
1. A spray ionization device, comprising:
a first tube including a first channel through which a liquid can flow, the first tube including a first outlet for ejecting the liquid at one end;
a second tube surrounding the first tube with a gap and including a second channel through which a gas can flow, the second tube including a second outlet at the one end, the second channel being defined by an outer circumferential surface of the first tube and an inner circumferential surface of the second tube; and an electrode which extends within the first channel of the first tube from an opposite end to the first end, and is arranged so that a leading end is the same position as the first outlet or further toward the opposite end than the first outlet, the electrode being capable of applying voltage to the liquid by way of a power source connected to the electrode, wherein the second channel includes a constriction portion, and a channel area of the second channel progressively decreases from the opposite end to the constriction portion, at the one end, the second outlet is arranged further downstream than the first outlet, at least a portion of the inner circumferential surface of the second tube has a diameter that progressively decreases toward the second outlet, and a diameter of the inner circumferential surface of the second outlet is equal to or greater than an opening diameter of the first outlet, and electrically charged droplets of the liquid can be ejected from the second outlet, the spray ionization device, further comprising: a third tube between the first tube and the second tube, the third tube surrounding the first tube and including a third outlet at the one end, wherein the second channel through which the gas can flow is defined by an outer circumferential surface of the third tube and the inner circumferential surface of the second tube, at the one end, a tip of the third tube is arranged further toward the opposite end than the first outlet, and at a tip at the one end of the third tube, a gap between an inner circumferential surface of the third tube and the outer circumferential surface of the first tube is blocked.

2. The spray ionization device according to claim 1, wherein the first outlet of the first tube has an opening diameter smaller than the diameter of the inner circumferential surface of the second tube in the constriction portion.

3. The spray ionization device according to claim 1, wherein the third tube includes an other constriction portion formed by a tip of the outer circumferential surface at the one end of the third tube and the inner circumferential surface of the second tube.

4. The spray ionization device according to claim 3, wherein the second tube is formed such that at least the portion of the inner circumferential surface of the second tube has the diameter that progressively decreases from a portion of the other constriction portion toward the second outlet.

5. The spray ionization device according to claim 1, wherein, at a tip at the one end of the third tube, a dielectric material fills a gap between an inner circumferential surface of the third tube and the outer circumferential surface of the first tube.

6. The spray ionization device according to claim 1, further comprising: a source of the gas; and a heating unit for heating the gas between the source and a supply port provided at an opposite end of the first tube.

7. The spray ionization device according to claim 1, further comprising:

a high-voltage power source connected to the electrode, wherein the high-voltage power source applies voltage in a range of 0.5 kV to 10 kV to the electrode.

8. The spray ionization device according to claim 1, further comprising: a fourth tube surrounding the second tube with a gap and including a third channel through which a second gas can flow, the fourth tube including a fourth outlet at the one end, the third channel being defined by the outer circumferential surface of the second tube and an inner circumferential surface of the fourth tube.

9. The spray ionization device according to claim 8, wherein, at the one end, the fourth outlet is arranged further toward the tip than the second outlet, and an inner circumferential surface of the fourth tube has a diameter that at least progressively decreases toward the fourth outlet.

10. The spray ionization device according to claim 8, further comprising: a second heating unit for heating the second gas or electrically charged droplets of the liquid ejected from the second outlet together with the second gas enveloping the electrically charged droplets of the liquid.

11. The spray ionization device according to claim 1, wherein the spray ionization device is used in surface coating.

12. The spray ionization device according to claim 1, wherein the spray ionization device is used for space processing utilizing sterilization, deodorization, dust collection, and chemical reactions, by gas-phase or spatial chemical reactions by spraying of the electrically charged droplets.

13. The spray ionization device according to claim 1, wherein the spray ionization device is for an analysis device.

* * * * *